(12) United States Patent
Reed et al.

(10) Patent No.: US 10,946,205 B2
(45) Date of Patent: *Mar. 16, 2021

(54) IMPLANTABLE HEAD MOUNTED NEUROSTIMULATION SYSTEM FOR HEAD PAIN

(71) Applicant: NUXCEL, INC., Santa Clara, CA (US)

(72) Inventors: Kenneth Lyle Reed, Dallas, TX (US); Robert Raymond Bulger, Dallas, TX (US)

(73) Assignee: NUXCEL, INC., Santa Clara, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 15/979,165

(22) Filed: May 14, 2018

(65) Prior Publication Data
US 2018/0256903 A1 Sep. 13, 2018

Related U.S. Application Data

(63) Continuation of application No. 14/717,912, filed on May 20, 2015, now Pat. No. 9,974,968, which is a
(Continued)

(51) Int. Cl.
*A61N 1/375* (2006.01)
*A61N 1/378* (2006.01)
(Continued)

(52) U.S. Cl.
CPC ........... *A61N 1/375* (2013.01); *A61N 1/0504* (2013.01); *A61N 1/0526* (2013.01);
(Continued)

(58) Field of Classification Search
CPC .... A61N 1/3787; A61N 1/0529; A61N 1/375; A61N 1/37211; A61N 1/37229;
(Continued)

(56) References Cited

U.S. PATENT DOCUMENTS

| | | |
|---|---|---|
| 3,727,616 A | 4/1973 | Lenzkes |
| 3,908,668 A | 9/1975 | Bolduc |

(Continued)

FOREIGN PATENT DOCUMENTS

| | | |
|---|---|---|
| AU | 2014340652 A1 | 6/2016 |
| CA | 2734775 A1 | 3/2010 |

(Continued)

OTHER PUBLICATIONS

Trentman et al., Greater Occipital Nerve Stimulation via the Bion Microstimulator: Implantation Technique and Stimulation Parameters Clinical Trial: NCT00205894, Pain Physician May/Jun. 2009, pp. 621-628 (Year: 2009).*

(Continued)

*Primary Examiner* — Catherine M Voorhees
(74) *Attorney, Agent, or Firm* — Schwegman Lundberg & Woessner, P.A.

(57) ABSTRACT

An implantable head-mounted unibody peripheral neurostimulation system is provided for implantation in the head for the purpose of treating chronic head pain, including migraine. The system may include an implantable pulse generator (IPG) from which multiple stimulating leads may extend sufficient to allow for adequate stimulation over multiple regions of the head, preferably including the frontal, parietal and occipital regions. A lead may include an extended body, along which may be disposed a plurality of surface metal electrodes, which may be sub-divided into a plurality of electrode arrays. A plurality of internal metal wires may run a portion of its length and connect the IPG's internal circuit to the surface metal electrodes. The IPG may include a rechargeable battery, an antenna, and an application specific integrated circuit. The IPG may be capable of functional connection with an external radiofrequency unit (Continued)

for purposes that may include recharging, diagnostic evaluation, and programming.

20 Claims, 6 Drawing Sheets

Related U.S. Application Data continuation of application No. 14/460,139, filed on Aug. 14, 2014, now Pat. No. 9,042,991.

(60) Provisional application No. 61/894,795, filed on Oct. 23, 2013.

(51) Int. Cl.
  *A61N 1/372* (2006.01)
  *A61N 1/05* (2006.01)
  *A61N 1/36* (2006.01)

(52) U.S. Cl.
  CPC ......... *A61N 1/0529* (2013.01); *A61N 1/0551* (2013.01); *A61N 1/36075* (2013.01); *A61N 1/3787* (2013.01); *A61N 1/37211* (2013.01); *A61N 1/37229* (2013.01); *A61N 1/37247* (2013.01)

(58) Field of Classification Search
  CPC ................ A61N 1/0551; A61N 1/0526; A61N 1/36075; A61N 1/0504; A61N 1/37247
  See application file for complete search history.

(56) References Cited

U.S. PATENT DOCUMENTS

| | | |
|---|---|---|
| 4,441,498 A * | 4/1984 | Nordling ............ A61N 1/37229 128/903 |
| 4,612,934 A | 9/1986 | Borkan |
| 4,793,353 A | 12/1988 | Borkan |
| 4,819,647 A | 4/1989 | Byers |
| 5,000,194 A | 3/1991 | Van Den Honert et al. |
| 5,037,497 A | 8/1991 | Stypulkowski |
| 5,215,086 A | 6/1993 | Terry, Jr. et al. |
| 5,279,292 A | 1/1994 | Baumann et al. |
| 5,545,219 A | 8/1996 | Kuzma |
| 5,569,307 A | 10/1996 | Schulman et al. |
| 5,615,100 A | 3/1997 | Radecker et al. |
| 5,733,313 A | 3/1998 | Barreras, Sr. et al. |
| 5,876,425 A | 3/1999 | Gord et al. |
| 5,905,646 A | 5/1999 | Crewson et al. |
| 6,016,449 A | 1/2000 | Fischell et al. |
| 6,088,619 A | 7/2000 | Hein et al. |
| 6,178,353 B1 | 1/2001 | Griffith et al. |
| 6,236,892 B1 | 5/2001 | Feler |
| 6,246,911 B1 | 6/2001 | Seligman |
| 6,456,883 B1 | 9/2002 | Torgerson et al. |
| 6,516,227 B1 | 2/2003 | Meadows et al. |
| 6,529,774 B1 | 3/2003 | Greene |
| 6,597,954 B1 | 7/2003 | Pless et al. |
| 6,606,521 B2 | 8/2003 | Paspa et al. |
| 6,618,623 B1 | 9/2003 | Pless et al. |
| 6,895,283 B2 | 5/2005 | Erickson et al. |
| 6,920,359 B2 | 7/2005 | Meadows et al. |
| 7,127,298 B1 | 10/2006 | He et al. |
| 7,171,273 B2 | 1/2007 | Shaquer |
| 7,319,906 B2 | 1/2008 | Kuzma et al. |
| 7,437,197 B2 | 10/2008 | Harris et al. |
| 7,499,755 B2 | 3/2009 | Cross, Jr. |
| 7,599,743 B2 | 10/2009 | Hassler, Jr. et al. |
| 7,676,273 B2 | 3/2010 | Goetz et al. |
| 7,706,892 B2 | 4/2010 | Colvin et al. |
| 7,729,781 B2 | 6/2010 | Swoyer et al. |
| 7,769,461 B2 | 8/2010 | Whitehurst et al. |
| 7,894,905 B2 | 2/2011 | Pless et al. |
| 8,027,735 B1 | 9/2011 | Tziviskos et al. |
| 8,030,798 B2 | 10/2011 | Seligman |
| 8,140,152 B2 | 3/2012 | John et al. |
| 8,165,678 B2 | 4/2012 | Forsberg et al. |
| 8,412,334 B2 | 4/2013 | Whitehurst et al. |
| 8,457,744 B2 | 6/2013 | Janzig et al. |
| 8,504,163 B1 | 8/2013 | Meadows |
| 8,509,876 B2 | 8/2013 | Karmarkar |
| 8,538,545 B2 | 9/2013 | Meskens |
| 8,543,212 B2 | 9/2013 | Merfeld et al. |
| 8,634,909 B2 | 1/2014 | Zimmerling et al. |
| 8,639,344 B2 | 1/2014 | Greenberg et al. |
| 8,639,391 B1 | 1/2014 | Alberth, Jr. et al. |
| 8,649,880 B1 | 2/2014 | Parker |
| 8,718,779 B2 | 5/2014 | Whitehurst et al. |
| 8,774,924 B2 | 7/2014 | Weiner |
| 8,812,113 B2 | 8/2014 | Mashiach |
| 8,958,880 B2 | 2/2015 | De Giorgio |
| 8,972,015 B2 | 3/2015 | Stack et al. |
| 9,020,589 B2 | 4/2015 | Torgerson |
| 9,031,662 B2 | 5/2015 | Leigh et al. |
| 9,042,991 B2 * | 5/2015 | Reed .................... A61N 1/3787 607/46 |
| 9,095,699 B2 | 8/2015 | Rosenberg et al. |
| 9,101,732 B2 | 8/2015 | Dadd et al. |
| 9,119,957 B2 | 9/2015 | Gantz et al. |
| 9,403,024 B2 | 8/2016 | Bunyan et al. |
| 9,421,387 B2 | 8/2016 | Hazard et al. |
| 9,498,635 B2 | 11/2016 | Dellamano et al. |
| 9,498,636 B2 | 11/2016 | Dellamano et al. |
| 9,539,432 B2 | 1/2017 | Dellamano et al. |
| 9,884,190 B2 | 2/2018 | Reed et al. |
| 9,889,308 B2 | 2/2018 | Dellamano et al. |
| 9,974,968 B2 * | 5/2018 | Reed .................... A61N 1/3787 |
| 10,258,805 B2 | 4/2019 | Reed et al. |
| 10,416,252 B2 | 9/2019 | Liu |
| 10,695,571 B2 | 6/2020 | Dellamano et al. |
| 2002/0032471 A1 | 3/2002 | Loftin et al. |
| 2002/0116042 A1 | 8/2002 | Boling |
| 2004/0215280 A1 | 10/2004 | Dublin et al. |
| 2005/0004637 A1 | 1/2005 | Singhal et al. |
| 2005/0027192 A1 | 2/2005 | Govari et al. |
| 2005/0030774 A1 | 2/2005 | Vazquez |
| 2005/0075696 A1 | 4/2005 | Forsberg et al. |
| 2005/0102006 A1 | 5/2005 | Whitehurst et al. |
| 2005/0182470 A1 | 8/2005 | Cross |
| 2005/0209667 A1 | 9/2005 | Erickson et al. |
| 2005/0288741 A1 | 12/2005 | Hassler et al. |
| 2006/0206166 A1 | 9/2006 | Weiner |
| 2006/0241717 A1 | 10/2006 | Whitehurst et al. |
| 2006/0247754 A1 | 11/2006 | Greenberg et al. |
| 2006/0293723 A1 | 12/2006 | Whitehurst et al. |
| 2007/0049988 A1 | 3/2007 | Carbunaru et al. |
| 2007/0073357 A1 | 3/2007 | Rooney et al. |
| 2007/0097719 A1 | 5/2007 | Parramon et al. |
| 2007/0112404 A1 | 5/2007 | Mann et al. |
| 2007/0203545 A1 | 8/2007 | Stone et al. |
| 2008/0039916 A1 | 2/2008 | Colliou et al. |
| 2008/0132979 A1 | 6/2008 | Gerber |
| 2008/0183253 A1 | 7/2008 | Bly |
| 2008/0268729 A1 | 10/2008 | Yomo et al. |
| 2008/0269716 A1 | 10/2008 | Bonde |
| 2008/0300657 A1 | 12/2008 | Stultz |
| 2009/0018619 A1 | 1/2009 | Skelton et al. |
| 2009/0058635 A1 | 3/2009 | LaLonde et al. |
| 2009/0069869 A1 | 3/2009 | Stouffer et al. |
| 2009/0209945 A1 | 8/2009 | Lobl et al. |
| 2009/0210028 A1 | 8/2009 | Rigaux |
| 2009/0216324 A1 | 8/2009 | Leigh et al. |
| 2009/0312769 A1 | 12/2009 | Dadd |
| 2010/0110741 A1 | 5/2010 | Lin et al. |
| 2010/0114249 A1 | 5/2010 | Wahlstrand et al. |
| 2010/0161004 A1 | 6/2010 | Najafi et al. |
| 2010/0174341 A1 | 7/2010 | Bolea et al. |
| 2010/0274313 A1 | 10/2010 | Boling et al. |
| 2010/0331922 A1 | 12/2010 | Digiore et al. |
| 2011/0009925 A1 | 1/2011 | Leigh et al. |
| 2011/0046699 A1 | 2/2011 | Mazanec |
| 2011/0093047 A1 | 4/2011 | Davis et al. |

(56) References Cited

U.S. PATENT DOCUMENTS

| | | | |
|---|---|---|---|
| 2011/0106220 A1* | 5/2011 | DeGiorgio | A61N 1/0456 607/72 |
| 2011/0112603 A1 | 5/2011 | Degiorgio et al. | |
| 2011/0172736 A1 | 7/2011 | Gefen et al. | |
| 2011/0190849 A1 | 8/2011 | Faltys et al. | |
| 2012/0071936 A1 | 3/2012 | Pianca et al. | |
| 2012/0078327 A1 | 3/2012 | Sloan et al. | |
| 2012/0078337 A1 | 3/2012 | Darley et al. | |
| 2012/0078338 A1 | 3/2012 | Sheraton | |
| 2012/0112556 A1 | 5/2012 | Forsell | |
| 2012/0197375 A1* | 8/2012 | Pianca | A61N 1/0534 607/148 |
| 2012/0215218 A1 | 8/2012 | Lipani | |
| 2012/0274270 A1 | 11/2012 | Dinsmoor et al. | |
| 2012/0277823 A1 | 11/2012 | Gerber et al. | |
| 2013/0057364 A1 | 3/2013 | Kesler et al. | |
| 2013/0085542 A1 | 4/2013 | Mashiach | |
| 2013/0085561 A1 | 4/2013 | Mashiach | |
| 2013/0110210 A1* | 5/2013 | North | A61N 1/0553 607/117 |
| 2013/0131754 A1 | 5/2013 | Sarvazyan | |
| 2013/0165996 A1* | 6/2013 | Meadows | A61N 1/0556 607/60 |
| 2013/0197613 A1 | 8/2013 | Kelly et al. | |
| 2013/0198531 A1 | 8/2013 | Hansen et al. | |
| 2013/0238067 A1 | 9/2013 | Baudino | |
| 2013/0282086 A1 | 10/2013 | McDonald et al. | |
| 2013/0289662 A1 | 10/2013 | Olson et al. | |
| 2013/0333918 A1 | 12/2013 | Lotfi | |
| 2014/0012349 A1 | 1/2014 | Zimmerling et al. | |
| 2014/0070808 A1 | 3/2014 | Reykowski et al. | |
| 2014/0142669 A1 | 5/2014 | Cook et al. | |
| 2014/0148883 A1 | 5/2014 | Stack et al. | |
| 2014/0222125 A1 | 8/2014 | Glenn et al. | |
| 2014/0292327 A1 | 10/2014 | Griswold et al. | |
| 2014/0303685 A1 | 10/2014 | Rosenberg et al. | |
| 2014/0343626 A1 | 11/2014 | Thenuwara et al. | |
| 2015/0025613 A1 | 1/2015 | Nyberg, II et al. | |
| 2015/0087892 A1 | 3/2015 | Tourrel et al. | |
| 2015/0112406 A1 | 4/2015 | Reed et al. | |
| 2015/0134036 A1 | 5/2015 | Moazen et al. | |
| 2015/0157862 A1 | 6/2015 | Greenberg et al. | |
| 2015/0280444 A1 | 10/2015 | Smith et al. | |
| 2015/0303806 A1 | 10/2015 | Madsen et al. | |
| 2015/0321004 A1 | 11/2015 | Reed et al. | |
| 2016/0008602 A1 | 1/2016 | Perryman et al. | |
| 2016/0030746 A1 | 2/2016 | Reed et al. | |
| 2016/0036244 A1 | 2/2016 | Griffith | |
| 2016/0082249 A1 | 3/2016 | Thenuwara et al. | |
| 2016/0114174 A1 | 4/2016 | Colvin et al. | |
| 2016/0114175 A1 | 4/2016 | Colvin et al. | |
| 2016/0114177 A1 | 4/2016 | Colvin et al. | |
| 2016/0235993 A1 | 8/2016 | Cryer et al. | |
| 2016/0242685 A1 | 8/2016 | Dehennis et al. | |
| 2017/0056646 A1 | 3/2017 | Sibary et al. | |
| 2017/0113054 A1 | 4/2017 | Dellamano et al. | |
| 2017/0252568 A1 | 9/2017 | Reed et al. | |
| 2018/0221664 A1 | 8/2018 | Reed et al. | |
| 2018/0236245 A1 | 8/2018 | Dellamano et al. | |
| 2019/0091480 A1 | 3/2019 | Reed et al. | |
| 2020/0289833 A1 | 9/2020 | Dellamano et al. | |

FOREIGN PATENT DOCUMENTS

| | | |
|---|---|---|
| CA | 2734775 C | 2/2015 |
| CA | 2927581 A1 | 4/2015 |
| EP | 0007157 | 1/1980 |
| EP | 3060293 A2 | 8/2016 |
| WO | 2009158389 | 12/2009 |
| WO | WO-2015060927 A2 | 4/2015 |
| WO | WO-2015060927 A3 | 7/2015 |
| WO | WO-2015060927 A4 | 9/2015 |

OTHER PUBLICATIONS

PCT: International Search Report and Written Opinion of PCT/US14/51235 (related application); dated Feb. 19, 2015; 24 pages, dated Feb. 19, 2015.

Weiner RL and Reed KL. Peripheral neurostimulation for control of intractable occipital neuralgia. Neuromodulation: Journal of the International Neuromodulation Society. 1999; 2: 217-21 Jan. 1, 1999.

Goadsby PJ and Spencer T. Current practice and future directions in the prevention and acute management of migraine. The Lancet Neurology. 2010; 9: 285-98. Jan. 1, 2010.

Dodick DW. Occipital nerve stimulation for chronic cluster headache. Advanced Studies in Medicine. 2003; 3: S569-S71. Jan. 1, 2003.

Saper JR, Dodick DW, Silberstein SD, McCarville S, Sun M and Goadsby PJ. Occipital nerve stimulation for the treatment of intractable chronic migraine headache: ONSTIM feasibility study. Cephalalgia: an international journal of headache. 2011; 31:271-85. Jan. 1, 2011.

Silberstein S, Dodick DW, Reed KL, et al. Safety and efficacy of peripheral nerve stimulation of the occiptial nerves for the management of chronic migraine. Cephalalgia: an international journal of headache. 2012. Jan. 1, 2012.

Slavin KV, Colpan ME, Munawar N, Wess C and Nersesyan H. Trigeminal and occipital peripheral nerve stimulation for craniofacial pain: a single-institution experience and review of the literature. Neurosurgical focus. 2006; 21: E5. Jan. 1, 2006.

Schwedt TJ, Dodick DW, Hentz J, Trentman TL and Zimmerman RS. Occipital nerve stimulation for chronic headache—long-term safety and efficacy. Cephalalgia: an international journal of headache. 2007; 27: 153-7. Jan. 1, 2007.

Reed KL, Black SB, Banta CJ, 2nd and Will KR. Combined occipital and supraorbital neurostimulation for the treatment of chronic migraine headaches: initial experience. Cephalalgia: an international journal of headache. 2010; 30: 260-71. Jan. 1, 2010.

Reed KL, Will KR, Chapman J and Richter E. Combined occipital and supraorbital neurostimulation for chronic migraine headaches [abst]. 15th Congress of the International Headache Society. Berlin, Germany: Cephalalgia, 2011, p. 98-9. Jan. 1, 2011.

Lipton RB, Goadsby PJ, Cady RK, et al. Prism study: occipital nerve stimulation for treatment-refractory migraine (p abs). Cephalalgia: an international journal of headache. 2009; 29: 30. Jan. 1, 2009.

Reed KL. Peripheral neuromodulation and headaches: history, clinical approach, and considerations on underlying mechanisms. Current pain and headache reports. 2012; 17: 25-35. Jan. 1, 2012.

Mueller OM, Gaul C, Katsarava Z, Diener HC, Sure U and Gasser T. Occipital nerve stimulation for the treatment of chronic cluster headache—lessons learned from 18 months experience. Central European neurosurgery. 2011; 72: 84-9. Jan. 1, 2011.

Medtronic, Inc. Peripheral Nerve Stimulation: Percutaneous Lead Implantation Guide for Treatment of Chronic Pain Jan. 1, 1999.

European Patent Office, Extended European Search Report, No. EP 14 85 5587, dated May 24, 2017; Lins, Stephanie; 7 pages.

"U.S. Appl. No. 14/460,139, Examiner Interview Summary dated Feb. 20, 2015", 3 pgs.

"U.S. Appl. No. 14/460,139, Non Final Office Action dated Oct. 27, 2014", 21 pgs.

"U.S. Appl. No. 14/460,139, Notice of Allowance dated Apr. 6, 2015", 9 pgs.

"U.S. Appl. No. 14/460,139, Response filed Jan. 27, 2015 to Non Final Office Action dated Oct. 27, 2014", 18 pgs.

"U.S. Appl. No. 14/460,139, Supplemental Amendment filed Mar. 26, 2015", 12 pgs.

"U.S. Appl. No. 14/717,912, Corrected Notice of Allowability dated Apr. 3, 2018", 2 pgs.

"U.S. Appl. No. 14/717,912, Examiner Interview Summary dated Apr. 3, 2017", 3 pgs.

"U.S. Appl. No. 14/717,912, Final Office Action dated Dec. 21, 2016", 12 pgs.

"U.S. Appl. No. 14/717,912, Non Final Office Action dated May 26, 2016", 16 pgs.

(56) References Cited

OTHER PUBLICATIONS

"U.S. Appl. No. 14/717,912, Non Final Office Action dated Jul. 11, 2017", 13 pgs.
"U.S. Appl. No. 14/717,912, Notice of Allowance dated Mar. 26, 2018", 8 pgs.
"U.S. Appl. No. 14/717,912, Preliminary Amendment filed May 20, 2015", 7 pgs.
"U.S. Appl. No. 14/717,912, Response filed Jan. 9, 2018 to Non Final Office Action dated Jul. 11, 2017", 8 pgs.
"U.S. Appl. No. 14/717,912, Response filed Jun. 2, 2017 to Final Office Action dated Dec. 21, 2016", 9 pgs.
"U.S. Appl. No. 14/717,912, Response filed Nov. 28, 2016 to Non Final Office Action dated May 26, 2016", 13 pgs.
"U.S. Appl. No. 14/879,943, 312 Amendment filed Oct. 23, 2017", 14 pgs.
"U.S. Appl. No. 14/879,943, Non Final Office Action dated Oct. 6, 2016", 12 pgs.
"U.S. Appl. No. 14/879,943, Notice of Allowance dated May 26, 2017", 8 pgs.
"U.S. Appl. No. 14/879,943, Notice of Allowance dated Oct. 16, 2017", 9 pgs.
"U.S. Appl. No. 14/879,943, PTO Response to Rule 312 Communication dated Nov. 1, 2017", 2 pgs.
"U.S. Appl. No. 14/879,943, Response filed May 15, 2017 to Non Final Office Action dated Oct. 6, 2016", 14 pgs.
"U.S. Appl. No. 14/879,943, Response filed Sep. 7, 2016 to Restriction Requirement dated Sep. 2, 2016", 7 pgs.
"U.S. Appl. No. 14/879,943, Restriction Requirement dated Sep. 2, 2016", 5 pgs.
"U.S. Appl. No. 14/989,674, 312 Amendment filed Aug. 1, 2016", 10 pgs.
"U.S. Appl. No. 14/989,674, Examiner Interview Summary dated Jul. 7, 2016", 3 pgs.
"U.S. Appl. No. 14/989,674, Non Final Office Action dated Apr. 5, 2016", 19 pgs.
"U.S. Appl. No. 14/989,674, Notice of Allowance dated Jul. 27, 2016", 7 pgs.
"U.S. Appl. No. 14/989,674, Preliminary Amendment filed Jan. 18, 2016", 7 pgs.
"U.S. Appl. No. 14/989,674, PTO Response to Rule 312 Communication dated Aug. 11, 2016", 2 pgs.
"U.S. Appl. No. 14/989,674, Response filed Jul. 5, 2016 to Non Final Office Action dated Apr. 5, 2016", 25 pgs.
"U.S. Appl. No. 14/990,654, 312 Amendment filed Oct. 11, 2016", 9 pgs.
"U.S. Appl. No. 14/990,654, Non Final Office Action dated Apr. 15, 2016", 16 pgs.
"U.S. Appl. No. 14/990,654, Notice of Allowance dated Aug. 8, 2016", 8 pgs.
"U.S. Appl. No. 14/990,654, PTO Response to Rule 312 Communication dated Oct. 20, 2016", 2 pgs.
"U.S. Appl. No. 14/990,654, Response filed Jul. 14, 2016 to Non Final Office Action dated Apr. 15, 2016", 25 pgs.
"U.S. Appl. No. 14/990,678, 312 Amendment filed Oct. 11, 2016", 7 pgs.
"U.S. Appl. No. 14/990,678, Non Final Office Action dated Apr. 27, 2016", 16 pgs.
"U.S. Appl. No. 14/990,678, Notice of Allowance dated Sep. 6, 2016", 7 pgs.
"U.S. Appl. No. 14/990,678, PTO Response to Rule 312 Communication dated Oct. 21, 2016", 2 pgs.
"U.S. Appl. No. 14/990,678, Response filed Jul. 27, 2016 to Non Final Office Action dated Apr. 27, 2016", 24 pgs.
"U.S. Appl. No. 15/402,090, 312 Amendment filed Oct. 20, 2017", 3 pgs.
"U.S. Appl. No. 15/402,090, Non Final Office Action dated Mar. 6, 2017", 17 pgs.
"U.S. Appl. No. 15/402,090, Notice of Allowance dated Sep. 27, 2017", 8 pgs.
"U.S. Appl. No. 15/402,090, PTO Response to 312 Communication dated Nov. 1, 2017", 2 pgs.
"U.S. Appl. No. 15/402,090, Response filed Sep. 6, 2017 to Non Final Office Action dated Mar. 6, 2017", 28 pgs.
"U.S. Appl. No. 15/599,206, Non Final Office Action dated May 14, 2018", 8 pgs.
"U.S. Appl. No. 15/599,206, Notice of Allowance dated Dec. 4, 2018", 7 pgs.
"U.S. Appl. No. 15/599,206, Response filed Oct. 15, 2018 to Non Final Office Action dated May 14, 2018", 22 pgs.
"U.S. Appl. No. 15/890,020, Examiner Interview Summary dated Jan. 21, 2020", 4 pgs.
"U.S. Appl. No. 15/890,020, Final Office Action dated Jan. 2, 2020", 19 pgs.
"U.S. Appl. No. 15/890,020, Non Final Office Action dated Jun. 20, 2019", 15 pgs.
"U.S. Appl. No. 15/890,020, Response filed Nov. 20, 2019 to Non-Final Office Action dated Jun. 20, 2019", 9 pgs.
"U.S. Appl. No. 15/892,605, Final Office Action dated Dec. 11, 2019", 20 pgs.
"U.S. Appl. No. 15/892,605, Non Final Office Action dated Jul. 9, 2019", 17 pgs.
"U.S. Appl. No. 15/892,605, Notice of Allowance dated Feb. 24, 2020", 8 pgs.
"U.S. Appl. No. 15/892,605, Response filed Feb. 11, 2020 to Final Office Action dated Dec. 11, 2019", 11 pgs.
"U.S. Appl. No. 15/892,605, Response filed Nov. 12, 2019 to Non-Final Office Action dated Jul. 9, 2019", 12 pgs.
"Australian Application Serial No. 2014340652, First Examination Report dated Dec. 13, 2018", 2 pgs.
"Australian Application Serial No. 2014340652, Response filed Nov. 12, 2019 to First Examination Report dated Dec. 13, 2018", 69 pgs.
"Canadian Application Serial No. 2927581, Office Action dated Oct. 10, 2019", 4 pgs.
"International Application Serial No. PCT/US2014/051235, International Preliminary Report on Patentability dated May 6, 2016", 9 pgs.
"International Application Serial No. PCT/US2014/051235, Invitation to Pay Additional Fees mailed Dec. 10, 2014", 2 pgs.
"Modern Speech Recognition Approaches with Case Studies", InTech, Chapter 10 Cochlear Implant Stimulation Rates and Speech Perception, (Nov. 28, 2012), 41 pgs.
Bulger, Robert, et al., "Combined Supraorbital (SONS) and Occipital Nerve Stimulation (ONS) for Intractable Post-Herpetic Neuralgia", Neurology, 82, P7, (2014), 317.
Dodick, D, et al., "Chronic Migraine Study Investigators; Evidence for Long-Term Efficacy of Peripheral Nerve Stimulation of the Occipital Nerves in the Management of Chronic Migraine", Cephalalgia, 33, (2013), 58.
Dodick, David W, et al., "Safety and Efficacy of Peripheral Nerve Stimulation of the Occipital Nerves for the Management of Chronic Migraine: Long-Term Results from a Randomized, Multicenter, Double-Blinded, Controlled Study", Cephalalgia, (2014), 15 pgs.
Linder, S L, "Combined Occipital Nerve/Supraorbital Nerve Stimulation for Treatment of Refractory Headaches: Initial Adolescent Experience (Ages 12 to 17)", Cephalalgia, 31, (2011), 171.
Redl, Richard, "Fundamental Considerations for Very High Frequency Power Conversion", Electronic Feasibility Investigations, (Jan. 1, 2008), 24 pgs.
Reed, K L, et al., "Combined occipital and supraorbital neurostimulation for chronic migraine headaches in adolescents (Ages 14-19): A retrospective analysis of 23 consecutive patients", Cephalalgia. 33, (2013), 198.
Reed, K L, et al., "Combined occipital and supraorbital neurostimulation for chronic migraine headaches: A multicenter retrospective analysis of 171 consecutive patients", Cephalalgia, 33, (2013), 197-8.
Reed, K, et al., "Combined Occipital and Supraorbital Neurostimulation for Chronic Migraine Headaches: An Extended Case Series (Abstract)", Cephalalgia, 31, (2011), 98-9.

(56) References Cited

OTHER PUBLICATIONS

Reed, Ken L, "Concordant Occipital and Supraorbital Neurostimulation Therapy for Hemiplegic Migraine; Initial Experience; A Case Series", Neuromodulation, (2015), 7 pgs.
Reed, Ken L, "Peripheral Neuromodulation and Headaches: History, Clinical Approach, and Considerations on Underlying Mechanisms", Current pain and headache reports, 17, (2013), 305-18.
Reed, Kenneth, et al., "Combined concordant peripheral neurostimulation for chronic migraine headaches: A retrospective analysis of 188 consecutive patients (S41.001)", Neurology, 82, (2014), 1 pg.
Rooij, M, "eGaN FET based Wireless Energy Transfer Topology Performance Comparisons", (Jan. 1, 2015), 6 pgs.
Rooij, M, "eGaN FET based Wireless Energy Transfer Topology Performance Comparisons", (Jan. 1, 2015), 5 pgs.
Silberstein, S, et al., "Efficacy of occipital nerve stimulatior for the management of intractable, chronic migraine: Results from a prospective, multicenter, double-blinded Controlled study", Headache, 52, (2012), 866.
Silberstein, S, et al., "The Safety and Efficacy of Occipital Nerve Stimulation for the Management of Chronic Migraine", Cephalalgia, 31, (2011), 117.
Silberstein, Stephen D, et al., "Safety and Efficacy of Peripheral nerve Stimulation of the occipital Nerves for the Management of Chronic Migraine: Results from a Randomized, Multicenter, Double-Blinded, Controlled Study", Cephalagia, 32, (2012), 1165-79.
Sreelakshmi, V, et al., "An RF-FC Converter with Wide Dynamic Range Input Matching for Power Recovery Applications", International Journal of Advanced Research in Electrical, Electronics and Instrumentation Engineering, (Dec. 1, 2014), 14 pgs.
Weiner, Richard, et al., "Peripheral Neurostimulation to Control Intractable Occipital Neuralgia", Neurosurgery, 45, (1999), 696.
Weiner, Richard L, "Subcutaneous Neurostimulation for Intractable C2 Mediated Headaches", Journal of Neurosurgery, 45, (2001), 2 pgs.
U.S. Appl. No. 14/460,139 U.S. Pat. No. 9,042,991, filed Aug. 14, 2014, Implantable Head Mounted Neurostimulation System for Head Pain.
U.S. Appl. No. 14/717,912 U.S. Pat. No. 9,974,968, filed May 20, 2015, Implantable Head Mounted Neurostimulation System for Head Pain.
U.S. Appl. No. 14/879,943 U.S. Pat. No. 9,884,190, filed Oct. 9, 2015, Surgical Method for Implantable Head Mounted Neurostimulation System for Head Pain.
U.S. Appl. No. 15/890,020, filed Feb. 6, 2018, Surgical Method for Implantable Neurostimulation System for Pain.
U.S. Appl. No. 14/989,674 U.S. Pat. No. 9,498,635, filed Jan. 6, 2016, Implantable Head Located Radiofrequency Coupled Neurostimulation System for Head Pain.
U.S. Appl. No. 14/990,678 U.S. Pat. No. 9,539,432, filed Jan. 7, 2016, Implantable Head Located Radiofrequency Coupled Neurostimulation System for Head Pain.
U.S. Appl. No. 15/402,090 U.S. Pat. No. 9,889,308, filed Jan. 8, 2017, Implantable Head Located Radiofrequency Coupled Neurostimulation System for Head Pain.
U.S. Appl. No. 15/892,605, filed Feb. 9, 2018, Implantable Head Located Radiofrequency Coupled Neurostimulation System for Head Pain.
U.S. Appl. No. 14/990,654 U.S. Pat. No. 9,498,636, filed Jan. 7, 2016, Implantable Head Located Radiofrequency Coupled Neurostimulation System for Head Pain.
U.S. Appl. No. 15/599,206 U.S. Pat. No. 10,258,805, filed May 18, 2017, Surgical Method for Implantable Head Mounted Neurostimulation System for Head Pain.
U.S. Appl. No. 16/198,216, filed Nov. 21, 2018, Low Profile Head-Located Neurostimulator and Method of Fabrication.
"U.S. Appl. No. 15/890,020, Non Final Office Action dated Apr. 17, 2020", 8 pgs.
"U.S. Appl. No. 15/890,020, Response filed Mar. 20, 2020 to Final Office Action dated Jan. 2, 2020", 11 pgs.
"U.S. Appl. No. 15/890,020, Response filed Jul. 1, 2020 to Non Final Office Action dated Apr. 17, 2020", 8 pgs.
"Canadian Application Serial No. 2927581, Office Action dated Jun. 9, 2020", 4 pgs.
"Canadian Application Serial No. 2927581, Response filed Apr. 9, 2020 to Office Action dated Oct. 10, 2019", 8 pgs.
"U.S. Appl. No. 15/890,020, Non Final Office Action dated Jul. 29, 2020", 8 pgs.
"U.S. Appl. No. 15/890,020, Supplemental Notice of Allowability dated Sep. 25, 2020", 5 pgs.
"U.S. Appl. No. 16/198,216, Non Final Office Action dated Aug. 6, 2020", 15 pgs.
"Canadian Application Serial No. 2927581, Response filed Oct. 7, 2020 to Office Action dated Jun. 9, 2020", 17 pgs.

\* cited by examiner

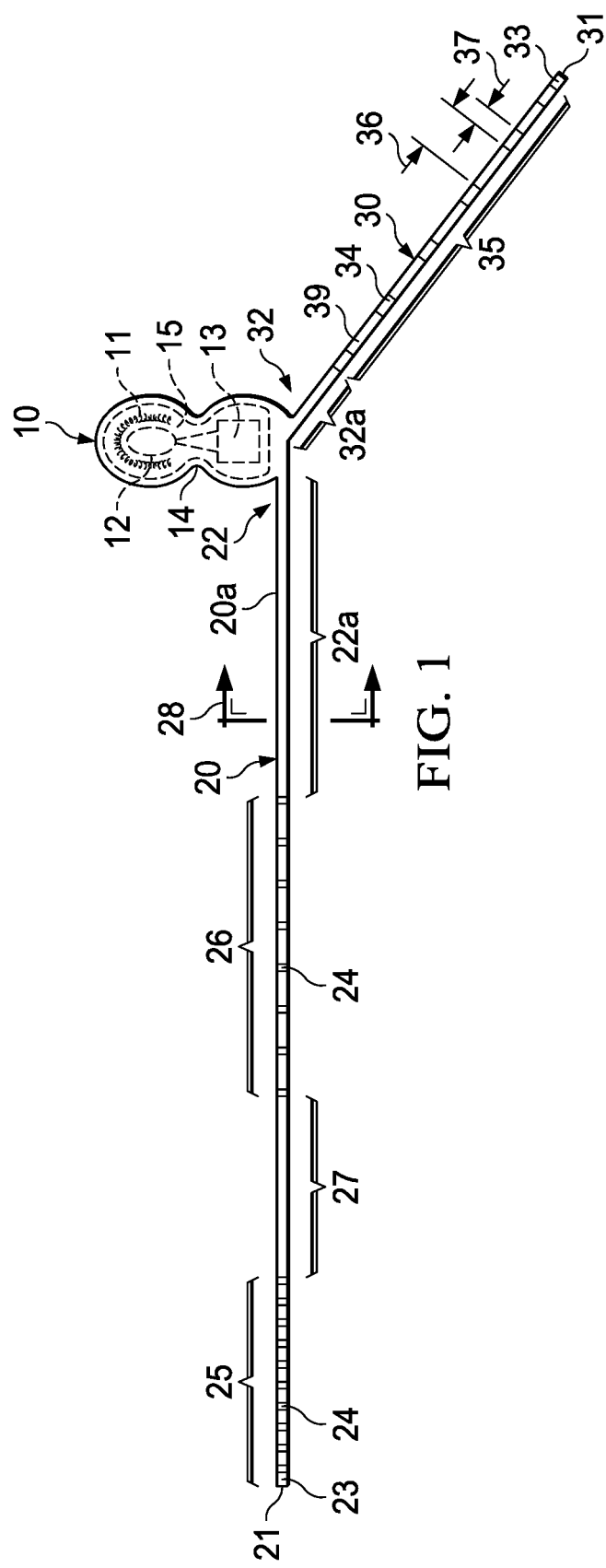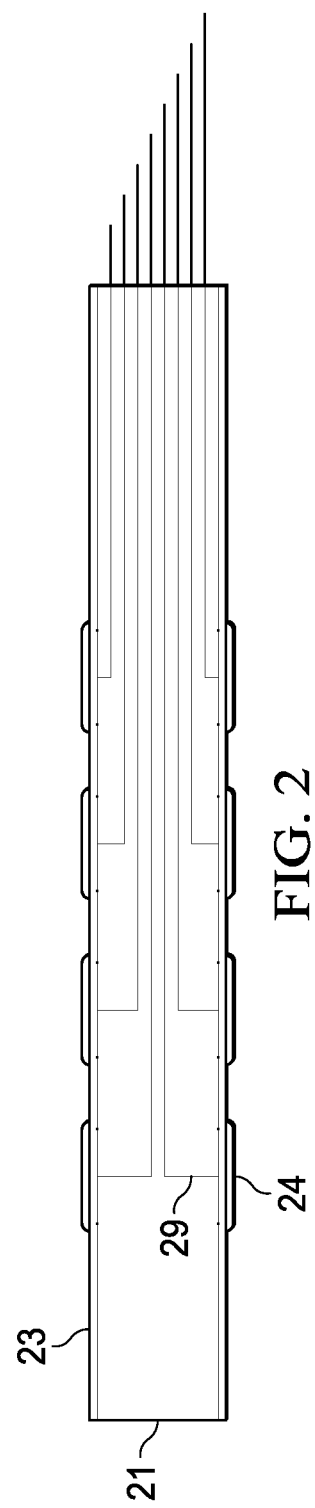

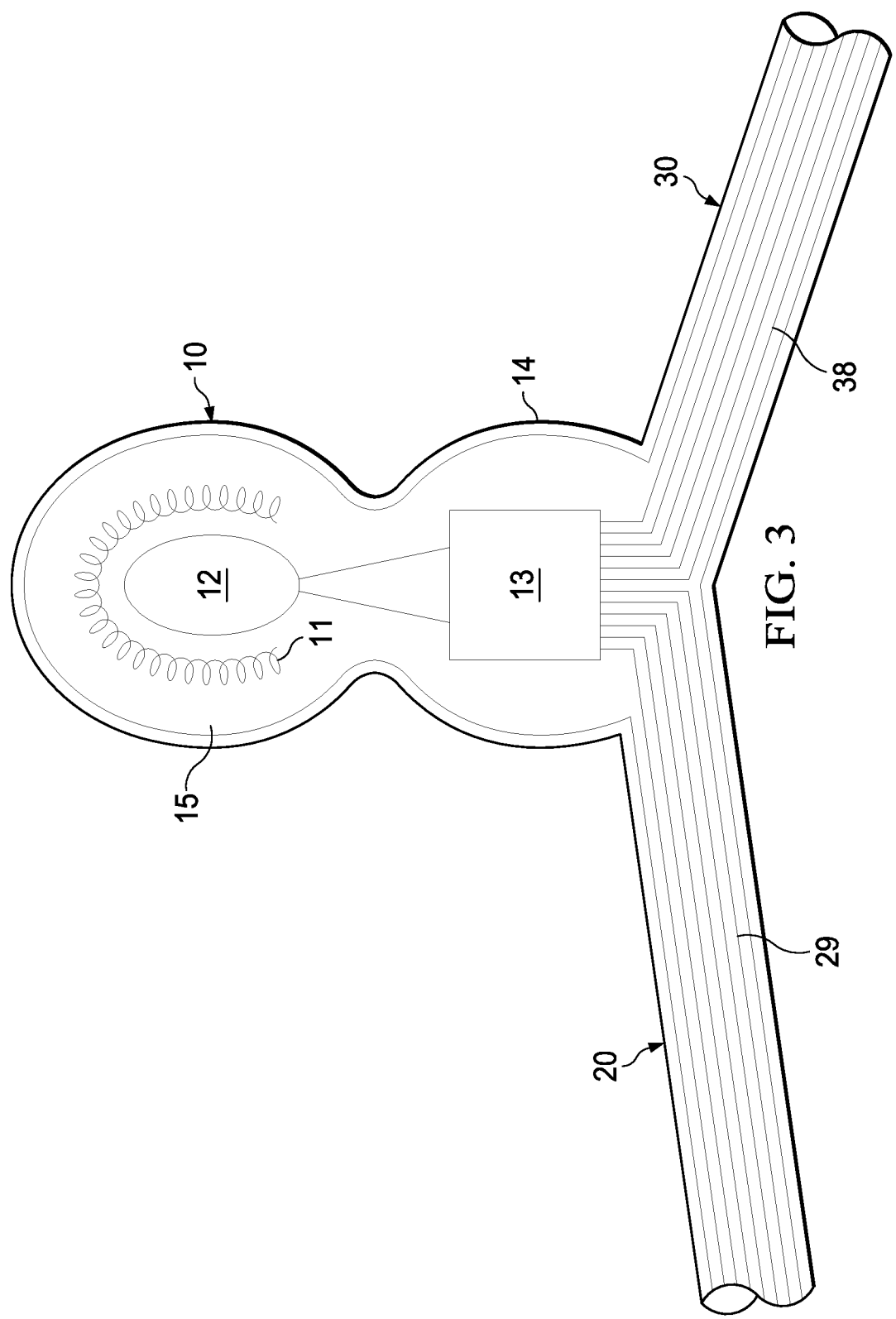

IMPLANTABLE HEAD MOUNTED NEUROSTIMULATION SYSTEM FOR HEAD PAIN

CROSS-REFERENCE TO RELATED APPLICATIONS

This application is a Continuation of U.S. patent application Ser. No. 14/717,912, filed on May 20, 2015, entitled IMPLANTABLE HEAD MOUNTED NEUROSTIMULATION SYSTEM FOR HEAD PAIN, which published on Nov. 12, 2015 as U.S. Patent Application Publication No. 2015-0321004. U.S. application Ser. No. 14/717,912 is a Continuation of U.S. patent application Ser. No. 14/460,139, filed Aug. 14, 2014, published on Apr. 23, 2015 as U.S. Patent Application Publication No. 2015-0112406, now U.S. Pat. No. 9,042,991, issued on May 26, 2015. Application Ser. No. 14/460,139 claims benefit of U.S. Provisional Application No. 61/894,795, filed Oct. 23, 2013, entitled IMPLANTABLE HEAD MOUNTED NEUROSTIMULATION SYSTEM FOR HEAD PAIN. U.S. patent application Ser. Nos. 14/717,912, 14/460,139 and 61/894,795, U.S. Patent Application Publication Nos. 2015-0321004 and 2015-0112406, and U.S. Pat. No. 9,042,991 are herein incorporated by reference in their entirety.

This application is related to U.S. patent application Ser. No. 14/460,111, filed Aug. 14, 2014, published on Feb. 19, 2015 as U.S. Patent Application Publication No. 2015-0051678. U.S. patent application Ser. No. 14/460,111 claims benefit of U.S. Provisional Application No. 61/865,893, filed Aug. 14, 2013, the specifications of which are herein incorporated by reference in their entirety.

TECHNICAL FIELD

The present disclosure relates generally to a fully head mounted implantable neurostimulation system and methods of treating migraine headaches and other forms of chronic head pain.

BACKGROUND

Neurostimulation systems comprising implantable neurostimulation leads are used to treat chronic pain. Conventional implantable peripheral neurostimulation leads are designed for placement in the spinal canal as part of a spinal cord stimulation system, and for the therapeutic purpose of treating various forms of chronic back and extremity pain.

SUMMARY

In various implementations, an implantable head-mounted, unibody peripheral nerve stimulation system may be configured for implantation of substantially all electronics, including an on-site battery, at or near the implanted electrodes on the skull. The system may include an implantable pulse generator (IPG) from which two neurostimulating leads may extend to a length sufficient to provide therapeutic neurostimulation unilaterally over the frontal, parietal and occipital regions of the hemicranium. The system may be operable to provide medically acceptable therapeutic neurostimulation to multiple regions of the head, including the frontal, parietal and occipital regions of the hemicranium, substantially simultaneously.

Each of the leads may include an extended lead body; a plurality of surface metal electrodes disposed along the lead body, which may be divided into two or more electrode arrays; and a plurality of internal electrically conducting metal wires running along at least a portion of the length of the lead body and individually connecting an internal circuit of the IPG to individual surface metal electrodes. The extended lead body may comprise a medical grade plastic. The IPG may include a rechargeable battery, an antenna coil, and an application specific integrated circuit (ASIC). The IPG may be configured for functionally connecting with an external radiofrequency unit. The external radiofrequency unit may be operable to perform various functions including recharging the rechargeable battery, diagnostically evaluating the IPG, and programming the IPG.

Implementations may include one or more of the following features. The IPG may be of proper aspect ratio with respect to the specific site of intended implantation in the head, such as an area posterior to and/or superior to the ear. There may be an external portable programming unit that is capable of achieving a radiofrequency couple to the implanted IPG. The IPG may have a rechargeable battery as a power source. The rechargeable battery may be inductively recharged through the skin.

Implementations may include one or more of the following features. A neurostimulating lead may not include a central channel for a stylet. A neurostimulating lead may have a smaller diameter than conventional leads.

Implementations may include one or more of the following features. The system may include the disposition of a sufficient plurality of surface electrodes over a sufficient linear distance along the neurostimulating leads to enable medically adequate therapeutic stimulation across multiple regions of the head, including the frontal, parietal, and occipital region of the hemicranium substantially simultaneously. The extended array of surface electrodes may be divided into two or more discrete terminal surface electrode arrays. The linear layout of the multiple surface electrode arrays may include at least one array positioned over the frontal region, at least one array positioned over the parietal region, and at least one array positioned over the occipital region.

Specific intra-array design features may include variations in the specific number of electrodes allotted to each group; the shape of the electrodes, e.g., whether the electrodes are cylindrical or flattened; the width of each electrode within each array, and the linear distance intervals of separation of the electrodes within each array.

Various implementations may include a plurality of connection ports that can be connected with a plurality of leads and thus allow for attaching additional leads.

In various implementations, methods of treating chronic pain may include methods of treating chronic head and/or face pain of multiple etiologies, including migraine headaches; and other primary headaches, including cluster headaches, hemicrania continua headaches, tension type headaches, chronic daily headaches; further including secondary headaches, such as cervicogenic headaches and other secondary musculoskeletal headaches.

In various implementations, methods of treating chronic pain may include methods of treating head and/or face pain of multiple etiologies, including neuropathic head and/or face pain, nociceptive head and/or face pain, and/or sympathetic related head and/or face pain.

In various implementations, methods of treating chronic pain may include methods of treating head and/or face pain of multiple etiologies, including greater occipital neuralgia, as well as the other various occipital neuralgias, supraorbital neuralgia, auriculo-temporal neuralgia, infraorbital neuralgia, and other trigeminal neuralgias, and other head and face neuralgias.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 1 depicts a side view of a head-mounted, unibody neurostimulator system for migraine and other head pain. The system features an implantable pulse generator (IPG) from which two neurostimulating leads extend—a Fronto-Parietal Lead (FPL) and an Occipital Lead (OL). Each lead includes a plurality of electrodes in a distribution and over a length to allow full unilateral coverage of the frontal, parietal, and occipital portions of the head.

FIG. 2 depicts a side view of a Frontal Electrode Array (FEA) with Internal Wires. The FEA is disposed over the distal portion (such as 8-10 cm) of the FPL, which anatomically places it over the frontal region, and specifically over the supraorbital nerve and other adjacent nerves of the region. In general the layout, disposition and connections of the Internal Wires and Surface Electrodes disposed over the Parietal Electrode Array (PEA) and the Occipital Electrode Array (OEA) are the same as that depicted for the FEA.

FIG. 3 depicts a side view of the Internal Wires exiting from the IPG's Internal Circuit enroute to the Surface Electrodes disposed over the FPL and the OL.

INDEX OF ELEMENTS

Figure 4:
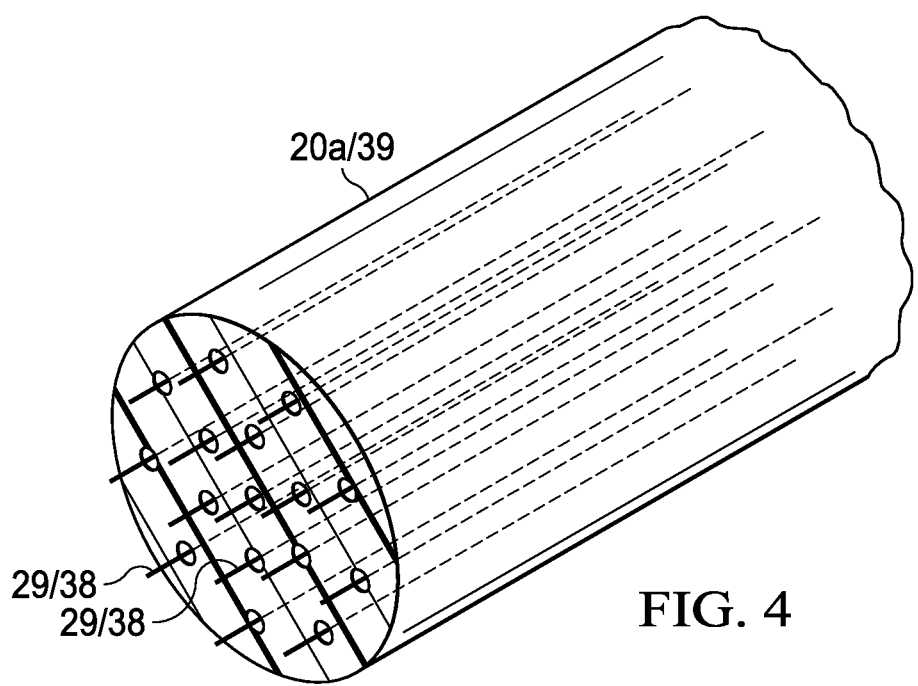
FIG. 4 depicts a cross-sectional view of a Lead Central Body comprising a Cylindrical Lead Body (with Internal Wires) between the IPG Internal Circuit and the Lead Surface Electrodes.

10: Implantable Pulse Generator
11: Antenna
12: Battery
13: Application Specific Integrated Circuit
14: Medical Plastic Cover
20: Fronto-Parietal Lead
20a: Plastic Body Member
21 Distal End
22: Proximal End
22a: Proximal Lead Segment
23: Distal Non-Stimulating Tip
24: Surface Metal Electrode
25: Frontal Electrode Array
26: Parietal Electrode Array
27: Inter-Array Interval
28 Point of Cross Section FIG. 4
29 Lead Internal Wire
30 Occipital Lead
31 Distal End
32 Proximal End
32a Proximal Lead Segment
33 Distal Non-Stimulating Tip
34 Surface Metal Electrode
35 Occipital Electrode Array
36 Interelectrode Distance
37 Surface Electrode Width
38 Lead Internal Wire
39 Plastic Body Member
50 Occipital Region of Head
51 Greater Occipital Nerve
52 Lesser Occipital Nerve
53 Third Occipital Nerve
60 Parietal Region of Head
61 Auriculotemporal Nerve
70 Frontal Region of Head
71 Supraorbital Nerve

DETAILED DESCRIPTION

Referring now to the drawings, wherein like reference numbers are used herein to designate like elements throughout, the various views and embodiments of implantable head mounted neurostimulation system for head pain are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

A. Introduction

The present disclosure provides a fully head mounted implantable peripheral neurostimulation system designed for the treatment of chronic head pain. It incorporates multiple elements and features that take into account the unique anatomic, physiologic, and other related challenges of treating head pain with implantable neurostimulation, thereby greatly improving on therapeutic response, patient safety, medical risk, and medical costs, which combine to improve overall patient satisfaction.

Prior implantable peripheral neurostimulation systems and components, including leads and pulse generators, have been designed and developed specifically as spinal cord stimulator systems and for the specific therapeutic purpose of treating chronic back and extremity pain. Over the years, these spinal cord stimulators were ultimately adopted and adapted for use as implantable peripheral nerve stimulators for the treatment of migraine headaches, and other forms of chronic head pain; however, they were so utilized with full recognition of the inherent risks and limitations given that they were developed only to address, and accommodate to, the unique anatomic and physiologic features of the back and chronic back pain.

U.S. Provisional Patent Application Ser. No 61/865,893 describes the manifold problems associated with the application of spinal cord stimulators for head pain as fundamentally due to design flaws associated with, and inherent to, the use of an implantable therapeutic device in an area of the body that it was not designed for.

Indeed, the anatomy of the head, and the pathophysiology of headaches, and other forms of head pain, are so significantly different from the anatomy of the spinal canal, and pathophysiology of chronic back pain, that when spinal cord stimulators are utilized for cranial implants, the clinical problems associated with these differences manifest themselves. Importantly, these well-documented problems are clinically very significant and include issues of patient safety and satisfaction, the risk of an inadequate, or suboptimal, therapeutic response; and issues with patient comfort and cosmetics; as well as a recognized increased risk of surgical complications and technical problems.

These medical issues stem from the design of conventional leads and the IPG. Conventional lead designs include a relatively large diameter, a cylindrical shape, (often) inadequate length and the necessity of implanting the IPG in the torso and distant from the distal leads, and a number and disposition of the surface electrodes and active lead arrays that do not match the requirements. A cylindrical lead of relatively large diameter results in increased pressure on, and manifest tenting of, the overlying skin, particularly of the forehead. Because conventional leads are of inadequate length to extend from the head to the IPG implant site, commonly in the lower back, abdomen, or gluteal region, lead extensions are often employed, and there are attendant risks of infection, local discomfort, and cosmetic concerns.

With respect to prior leads: 1) There is only a single array of electrodes, with common lead options including 4, 8, or 16 electrodes disposed over that single array; 2) The array is relatively short with most leads having an array of from 5-12 cm in length; 3) Within this single array, the individual electrodes are disposed uniformly with constant, equal inter-electrode distances. This results in the need to implant multiple (often four or more) of the conventional leads to adequately cover the painful regions of the head.

There are several practical clinical outcomes that result from the use of prior leads for the treatment of chronic head pain. First, since they comprise a single, relatively short active array, the currently available leads provide therapeutic stimulation to only a single region of the head; that is, they can provide stimulation to only the frontal region, or a portion of the parietal region, or a portion of the occipital region. Therefore, if a patient has pain that extends over multiple regions, then multiple separate lead implants are required—basically one lead implant is required for each unilateral region. A great majority of patients with chronic headaches experience holocephalic pain; that is they experience pain over the frontal and parietal and occipital regions bilaterally. Therefore, commonly these patients will need 4 to 7 leads implanted to achieve adequate therapeutic results (2 or 3 leads on each side).

Second, the need for multiple leads includes considerable added expense, and more importantly, added medical risk associated with adverse events attendant to the multiple surgical procedures. Such adverse events include an increased risk of infection, bleeding, and technical issues with the leads, e.g., lead fracture, lead migration, and local irritation.

Third, as the clinical database discloses, the inter-electrode spacing may be of central therapeutic significance. That is, for example, whereas commonly pain over the occipital region is consistently effectively treated by quadripolar leads (leads with four evenly spaced electrodes) that have the electrodes relatively widely spaced apart (approximately a cm or more apart), clinically it is often found that electrodes configurations that are more narrowly spaced may be more effective over the supraorbital nerve and regions. Thus, a quadripolar lead that has the electrodes only 1-2 mm apart may be more effective in this region, as it allows for more precise control of the delivered electrical pulse wave delivery.

Inter-electrode spacing is also of therapeutic significance. For example, whereas pain over the occipital region is commonly treated effectively by systems incorporating relatively widely-spaced quadripolar leads (four electrodes at approximately 1 cm or more intervals), more narrowly spaced contacts are often more effective over the supraorbital region.

When an IPG implant designed for spinal cord stimulation systems is employed as a peripheral nerve stimulator for head pain, several outcomes result. First, the IPG is implanted at a considerable anatomic distance for the cranial lead implants. Indeed, the leads must pass from their distal cranial implant positions across the cervical region and upper back to the IPG implant location, which are most commonly in the lower back, lower abdomen, or gluteal region. The leads must cross multiple anatomic motion segments, including the neck and upper back and/or chest at a minimum, and commonly include the mid back, lower back and waist segments, as well. The simple motions of normal daily life produce adverse tension and torque forces on the leads across these motion segments, which in turn increases the risk of various outcomes, including lead migration and/or lead fracture. In addition, the relatively large size of a spinal cord stimulator IPG contributes to local discomfort, cosmetic concerns, and increased risk of infection that may become larger and harder to treat in proportion to the size of the IPG pocket.

The present disclosure is directed to an implantable head-mounted unibody peripheral neurostimulation system that includes an IPG from which two neurostimulating leads extend to a length sufficient to allow for therapeutic neurostimulation unilaterally over the frontal, parietal and occipital regions of the head.

The present disclosure addresses and effectively solves problems attendant to publically available leads. The most important of these is the fact that current leads can only adequately stimulate a single region of the head due to design element flaws associated with terminal surface electrode number and disposition. The disclosure additionally addresses and solves other problems inherent with the currently available leads, including problems with cosmetics and patient comfort, particularly over the frontal regions, due the uncomfortable pressure placed on the skin of the forehead, due the cylindrical shape and relatively large diameter of the distal portion of the lead. Finally, the lead of the present disclosure solves the currently available leads' problem of inadequate lead length to reach a gluteal location of the implantable pulse generator, which therefore necessitates the additional risk and expense of further surgery to implant lead extensions.

In one aspect, the implantable, head-mounted, neurostimulation system for head pain is operable for implantation in the head, and to provide neurostimulation therapy for chronic head pain, including chronic head pain caused by migraine and other headaches, as well as chronic head pain due other etiologies. The peripheral neurostimulator system disclosed herein takes into account unique anatomic features of the human head, as well as the unique, or singular, features of the various pathologies that give rise to head pain, including migraine and other headaches, as well as other forms of chronic head pain. To date, all commercially available systems that have been clinically utilized for implantation as a peripheral neurostimulator system were actually originally designed specifically for placement in the epidural space, as part of a spinal cord stimulation system, for the therapeutic purpose of treating chronic back and/or extremity pain. Thus, there are currently no commercially available leads or fully system that have designs in the public domain, that have been designed and developed for use in the head and for head pain.

In another aspect, the implantable, head-mounted, neurostimulation system for head pain comprises multiple design features, including disposition of a sufficient plurality of surface electrodes over a sufficient linear distance along the distal lead, such as will result in lead that, as a single lead, is capable of providing medically adequate therapeutic stimulation over the entire hemicranium; that is, over the frontal, parietal, and occipital region substantially simultaneously. Currently available systems, which were designed specifically for epidural placement for chronic back pain, are capable of only providing stimulation over a single region; that is over either the frontal region alone, or the parietal region alone, or the occipital region alone.

In yet another aspect, the implantable, head-mounted, neurostimulation system for head pain comprises multiple design features, including the physical grouping of the extended array of surface electrodes into three or more discrete terminal surface electrode arrays. The linear layout of these two or more (preferably three or more) surface electrodes arrays is designed such that following implantation there would be at least one array positioned over the frontal region, at least one array positioned over the parietal region, and at least one array positioned over the occipital region. This feature further improves upon therapeutic effectiveness of the extended terminal surface electrode array sufficient for hemicranial stimulation by allowing for more precise control of the therapeutic neurostimulation parameters.

In still another aspect, the implantable, head-mounted, neurostimulation system for head pain comprises multiple design features, including incorporating individual design features within each of the three or more individual surface electrode arrays; examples of such intra-array design features would include the specific number of electrodes allotted to each group; whether the electrodes are cylindrical or flattened; the width of each electrode within each array, and the linear distance intervals of separation of the electrodes within each array. This feature further improves upon therapeutic effectiveness of the extended terminal surface electrode array sufficient for hemicranial stimulation, and the grouping of these electrodes into three or more separate surface electrode arrays, by providing each specific array location a unique intra-array design that takes into account, and thereby seeks to optimizes, design elements that are known to be possibly or likely beneficial to the therapeutic end result, given the anticipated post-implant anatomic location of that array.

In yet another aspect, the implantable, head-mounted, neurostimulation system for head pain comprises multiple novel design features, including incorporating individual design features into a single lead design and thereby achieving additive benefits.

In still another aspect, an implantable, head-mounted, neurostimulation system for head pain results in a marked decrease in the number of separate lead implants required to adequately treat a single patient. A single implant will provide the same therapeutic anatomic coverage that it would take the implantation of three or four of the currently available leads; that is instead of the current which often calls for three or more leads to be implanted to provide adequate hemicranial coverage, the same anatomic region may be covered with a single stimulator lead implant. The lead provides extended coverage over the full hemicranium; that is achieving medically acceptable neurostimulation unilaterally over the frontal, parietal, and occipital regions simultaneously. In contrast, publically known leads are able to consistently provide medically acceptable neurostimulation therapy only over a single region; meaning that it would require three separate surgically placed lead implants to achieve the same therapeutic coverage of a single implant of a lead of the present disclosure. This will decrease the total number of surgeries required, as well as the extent of each individual surgery, for many patients.

In another aspect, the present disclosure is directed to a system that is fully localized to the head, which obviates the requirement of currently available systems of having long leads and extensions extending across the neck and back to IPG locations commonly in the low back and gluteal region, and thereby decreases the risk of problems attendant to such long leads and extensions, including discomfort, infection, technical extension issues such as fracture, and other morbidities. This ultimately results in a decreased number of surgeries required by a patient.

In other aspects the system may include one or more of the following features. A neurostimulating lead may not require a central channel for a stylet. A neurostimulating lead may have a smaller diameter than currently available leads.

In other aspects the system may include one or more of the following features. The system may include the disposition of a sufficient plurality of surface electrodes over a sufficient linear distance along the system's leads to enable medically adequate therapeutic stimulation across multiple regions of the head, and preferably the entire hemicranium; that is, over the frontal, parietal, and occipital region simultaneously. The extended array of surface electrodes may be divided into two or more discrete terminal surface electrode arrays. The preferred linear layout of these multiple surface electrode arrays includes at least one array positioned over the frontal region, at least one array positioned over the parietal region, and at least one array positioned over the occipital region.

In other aspects intra-array design features may include variations in the specific number of electrodes allotted to each group; the shape of the electrodes, e.g., whether the electrodes are cylindrical or flattened; the width of each electrode within each array, and the linear distance intervals of separation of the electrodes within each array.

In other aspects, the system may a plurality of connection ports that can be connected with a plurality of leads and thus allow for attaching additional leads should they later be required.

In another aspect, an implantable, head-mounted, neurostimulation system for head pain comprises multiple design features; including features aimed at improving patient safety by improving the incidence of adverse events, including the risk of infection, as well as the risk and incidence of known technical problems associated with implanted leads, including lead migration and lead fracture, amongst others. The lead may comprise two or more (i.e. three or more) surface electrode arrays, each uniquely designed, that are disposed over a sufficient lead length to allow for medically acceptable therapeutic neurostimulator coverage of at least regions within the supraorbital, parietal, and occipital cranial regions. To achieve the same clinical coverage from a single implant, it would require three or more separately surgically implanted leads. Therefore, by reducing the number of surgical incisions, as well as the number of surgically implanted leads, the associated risks of adverse events are proportionally diminished.

In yet another aspect, an implantable, head-mounted, neurostimulation system for head pain may treat chronic head and/or face pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches; including neuropathic head and/or face pain, nociceptive head and/or face pain, and/or sympathetic related head and/or face pain; including greater occipital neuralgia, as well as the other various occipital neuralgias, supraorbital neuralgia, auriculotemporal neuralgia, infraorbital neuralgia, and other trigeminal neuralgias, and other head and face neuralgias.

In other aspects, an implantable, head-mounted, neurostimulation system for head pain may not require a central channel for stylet placement over its distal (frontal) portions. The lead may improve patient comfort and cosmetics by virtue of its relatively small diameter over the distal portions of the lead, partially due the lack of a central stylet channel, as well as due to a progressive decrease in the number of internal wires continuing after each terminal electrode. The lead may further improve cosmetic appearance and patient comfort by incorporating a flattened lead design for that portion of the lead expected to be over the frontal portion of the head.

Thus the present disclosure provides for a peripheral neurostimulation lead that is uniquely designed for implantation in the head as a therapy for chronic head pain, and is designed to solve the known design issues associated with current leads, as the lead of the present disclosure seeks to optimize the therapeutic response, improve patient comfort, improve cosmetics, reduce the number of surgical leads required, reduce medical risk, and reduce medical costs.

B. Overview

Turning now to the drawings, which depict the system and several of its components in various aspects and views, and in which similar reference numerals denote similar elements. The drawings illustrate an IPG from which two neurostimulating leads may extend to a length sufficient to allow for therapeutic neurostimulation unilaterally over the frontal, parietal and occipital regions. The leads include an extended plastic lead body; a plurality of surface metal electrodes disposed along the lead, which may be divided into two or more electrode arrays; a plurality of internal electrically conducting metal wires running along at least a portion of its length and individually connecting the IPG's internal circuit to individual surface metal electrodes. The implantable pulse generator includes a rechargeable battery, an antenna coil, and ASIC. The system may be operable to provide medically acceptable therapeutic neurostimulation to multiple regions of the head, including the frontal, parietal and occipital regions simultaneously, and three figures demonstrate various views of this feature as the lead is depicted in-situ.

C. Full Head-Mounted Neurostimulator System

FIG. 1 depicts a side view of a full neurostimulator system, which consists of an implantable pulse generator (IPG) 10 along with two unibody plastic lead extensions—a Fronto-Parietal Lead (FPL) 20 and an Occipital Lead (OL) 30 of adequate length to extend to roughly the midline of the forehead and to the midline at the cervico-cranial junction, respectively.

Figure 5:
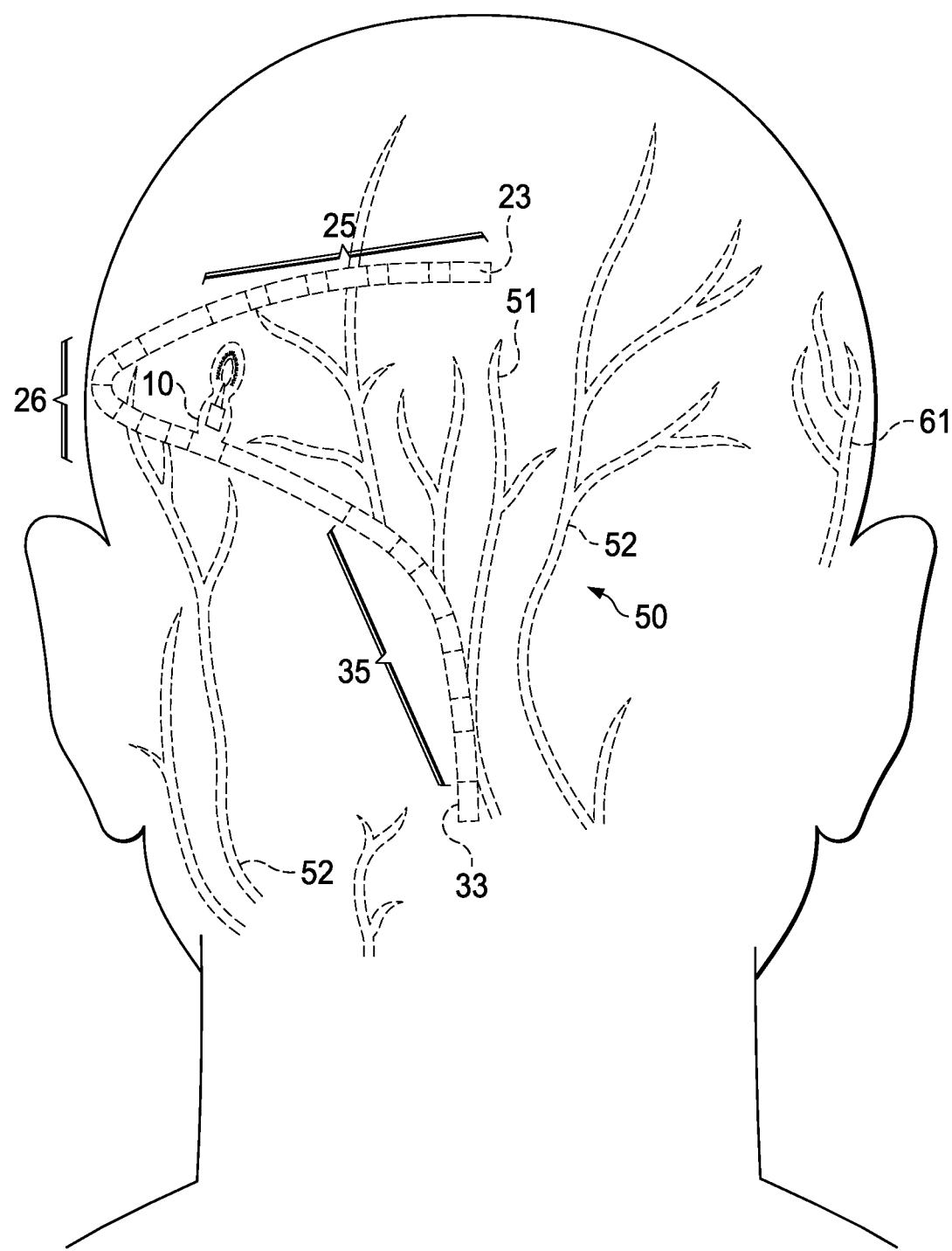
FIG. 5 depicts a rear view of a Head with a full Head-Mounted Neurostimulator System In-Situ. Prominent here is the OL depicted passing from the IPG caudally and medially across the occipital region, whereby the OEA is disposed in a fashion to cross over and cover the major associated nerves—primarily the greater occipital nerve, but typically including the lessor and/or third occipital nerve as well. Also depicted are the PEA and the FEA of the FPL as they cross and cover the primary nerves of the Parietal Region, including the auriculo-temporal nerve, and the Frontal Region, including the supraorbital nerve.
Figure 6:
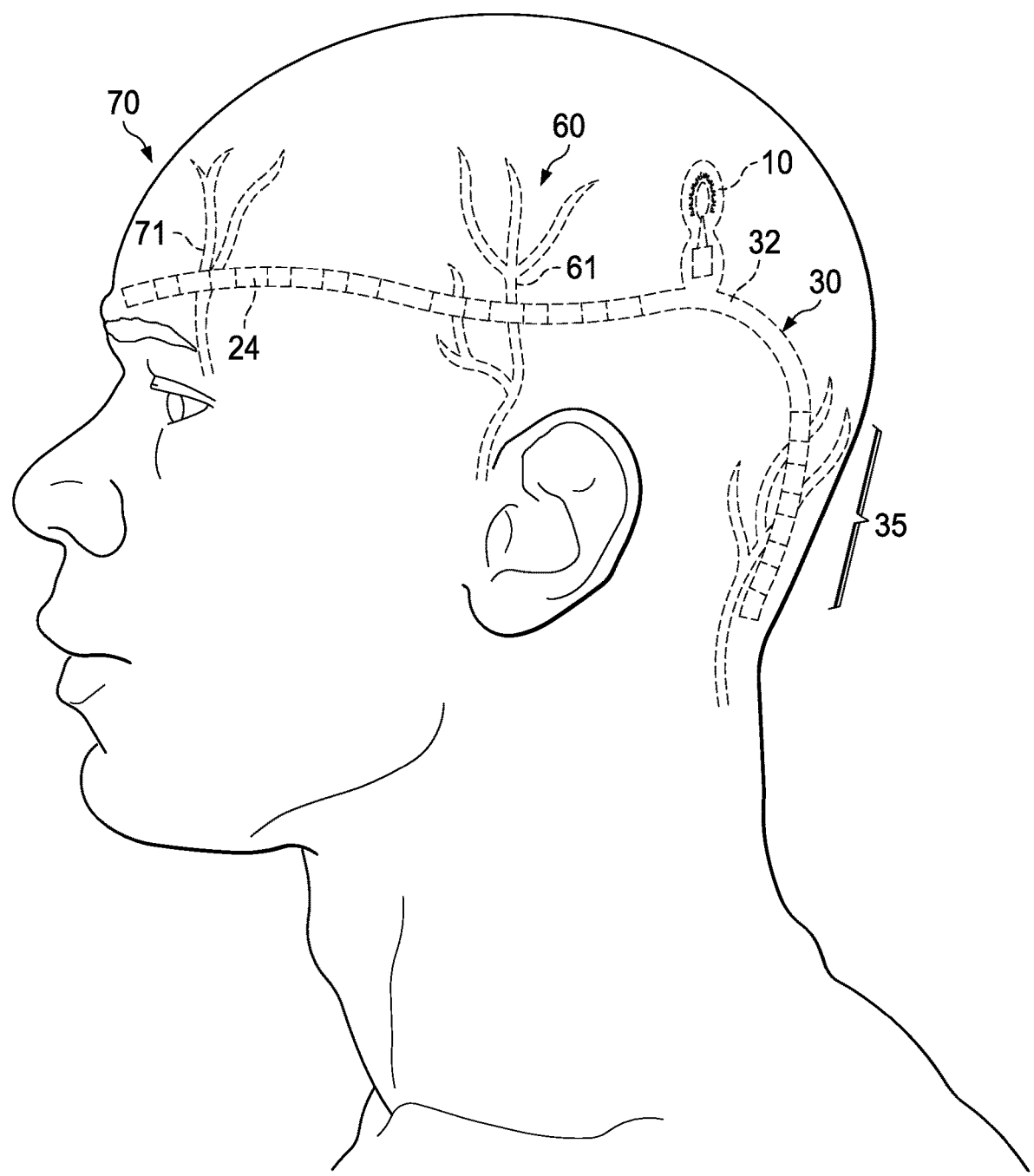
FIG. 6 depicts a side view of a Head with a full Head-Mounted Neurostimulator System In-Situ. Prominent here is the PEA, as it covers a portion of the Parietal Region and the major associated nerves, including the auriculo-temporal nerve, as well as adjacent cutaneous nerves. Also depicted are the courses of the distal portion of the FPL and the OL, as they pass over and cover the associated nerves of the Frontal (Supraorbital) and Occipital Regions.
Figure 7:
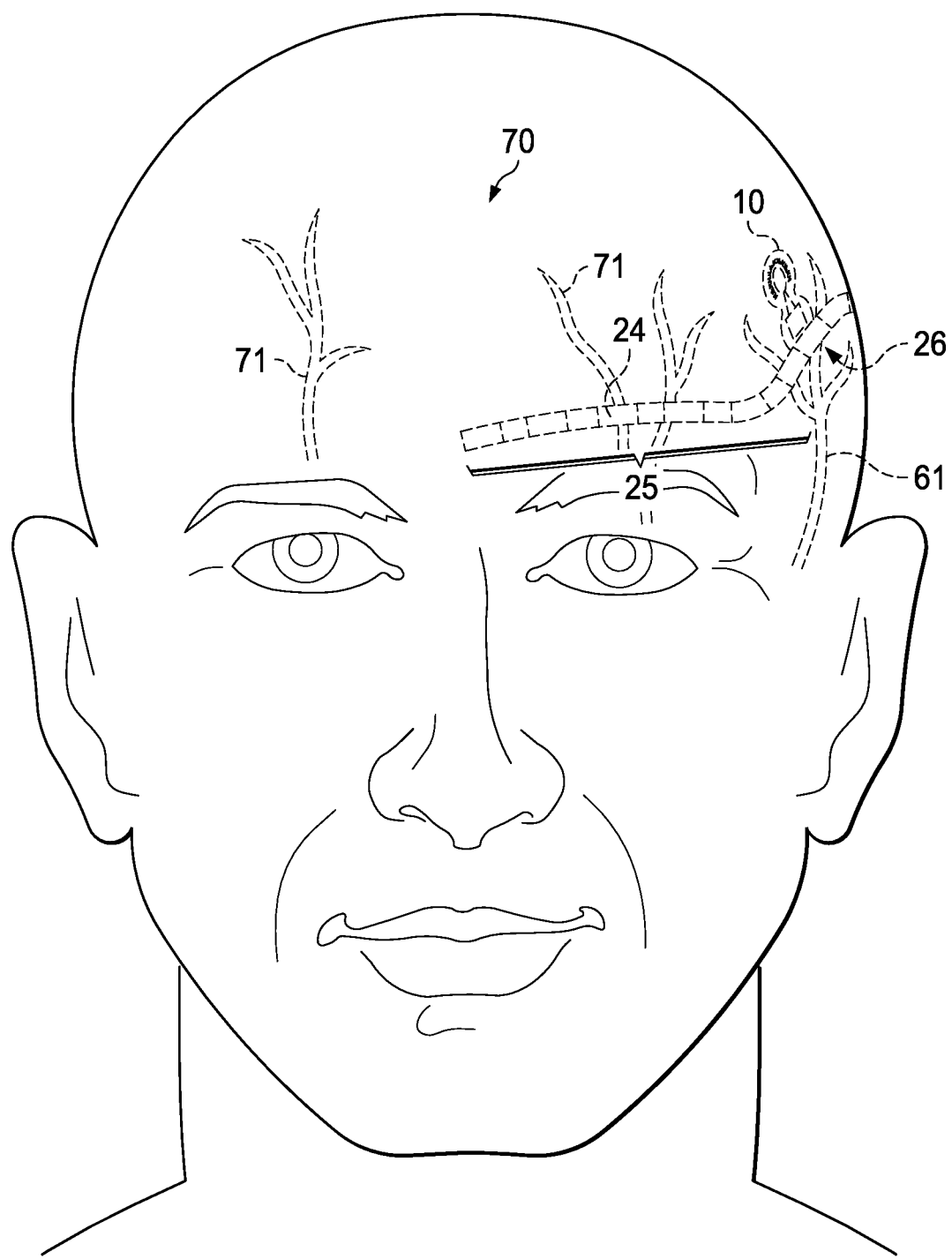
FIG. 7 depicts a front view of a Head with a full Head-Mounted Neurostimualtor System In-Situ. Prominent here is the FEA, as it covers a portion of the Frontal (Supraorbital) Region and the major associated nerves—primarily the supraorbital nerve, but also commonly the greater trochlear nerve, as well as adjacent nerves. Also depicted is the course of the parietal portion of the FL.

FIGS. 5, 6 and 7 depict posterior, lateral and frontal views of the system in-situ. The unit is demonstrated in an implant position where the IPG 10 is posterior and cephalad to the pinna of the ear. The drawings demonstrate the FPL 20 passing over the parietal 60 and frontal 70 regions of the head, including auriculotemporal nerve 61 and supraorbital nerve 71, in a manner that places the FEA over the supraorbital nerve and the PEA over the auriculotemporal nerve. The OL 30 is shown passing caudally and medially over the occipital region of the head 50 such that the OEA 35 cross over the greater occipital nerve 51, the lesser occipital nerve 52, and the third occipital nerve 53.

D. Fronto-Parietal Lead

Continuing with FIG. 1, the FPL as part of the unibody construction, extends from the IPG. The FPL comprises a plastic body member 20a and a set of internal conducting wires 29.

The plastic body member 20a is an elongated, cylindrical, flexible member, which may be formed of a medical grade plastic polymer. It has a proximal end 22, a distal end 21, and may be conceptually divided into five segments along its linear dimension. Progressing from the proximal end 22, these segments sequentially include a proximal lead segment (PLS) 22a, a parietal electrode array (PEA) 26, an inter-array interval 27, a frontal electrode array (FEA) 25, and a distal non-stimulating tip 23.

The lead internal wires 29 pass along the interior of the plastic body member as depicted in FIG. 4.

E. Frontal Electrode Array

Continuing with FIG. 1, the FEA 25 consists of a plurality of surface metal electrodes (SME) 24 uniformly disposed over a portion of the distal aspect of the FPL 20. Lead internal wires 29 connect to the SME 24 as depicted in FIG. 2, which represents the distal four SME 24 of the lead.

F. Parietal Electrode Array

Returning to FIG. 1, the PEA 26 consists of a plurality of SME 24 uniformly disposed along a linear portion of the FPL. The PEA 26 is separated along the FPL from the FEA by an inter-array interval 27. It is separated only the lead from the IPG by the PLS 22a. The lead internal wires 29 connect to the individual SME 24 of the PEA in the same fashion as the do with the SME of the FEA as shown in FIG. 2.

G. Occipital Lead

Continuing with FIG. 1, the occipital lead (OL) 30 as part of the unibody construction, extends from the IPG 10. It comprises a plastic body member 39 and a set of lead internal wires 38 that pass through the central cylinder of the lead to connect to a series of SME 34, each of surface electrode width 37, that are uniformly disposed at an inter-electrode distance 36 from each other along a portion of the length of the lead. These lead internal wires 38 pass and connect in the same manner as described above for the SME 24 of the FEA 25 as depicted in FIG. 2 and FIG. 4.

The plastic body member 39 is an elongated, cylindrical, flexible member, which may be formed of a medical grade plastic polymer. It has a proximal end 32 and a distal end 31. Progressing along the lead from the proximal end 32, these segments sequentially include a proximal lead segment (PLS) 32a, an occipital electrode array (OEA) 35, and a distal non-stimulating tip 33.

H. Occipital Lead Array

As depicted in FIG. 1, the OEA 35 consists of a plurality of surface metal electrodes (SME) 34 uniformly disposed over a portion OL 30. Lead internal wires 38 connect to the SME 24 in the same fashion as depicted for the FEA as shown in FIG. 2.

I. Implantable Pulse Generator

Referring to FIG. 1 and FIG. 3, the three primary physical and functional components of the IPG 10 include a rechargeable battery 12, an antenna 11, and an application specific integrated circuit (ASIC) 13, along with the necessary internal wire connections amongst these related components, as well as to the incoming lead internal wires 29, 39. These individual components may be encased in a can made of a medical grade metal and plastic cover 24, which itself transitions over the exiting FPL 20 and OL 30.

K. Connections of Main Elements and Sub-Elements

The system may include a unibody construction to provide physical and functional continuity of the related components and sub-components.

The overall mechanistic purpose of an implantable neurostimulation system is to generate and conduct a prescribed electrical pulse wave from an IPG 10 down a set of lead internal wires 29, 38 running a portion of the length of the lead to specified programmed set of SME 24, 34, whereby the current is then conducted by tissue and/or fluid to an adjacent, or nearby, set of one or more SME 24, 34, which in turn passes the signal proximally down the lead wire 29, 38 back to the IPG 10 and its ASIC 13, thus completing the circuit.

L. First Embodiment

The first embodiment provides for a lead that incorporates one or more of the features outlined above and includes a head-mounted, unibody neurostimulating system comprising an IPG 10 and at least two neurostimulating leads (FPL 20 and OL 30). The system may be implanted in a manner such that the IPG 10 and two leads 20, 30 are disposed as illustrated in FIG. 5, FIG. 6 and FIG. 7. The IPG 10 is capable of functionally connecting to and communicating with a portable programmer and an external power source for battery recharging.

In this embodiment, the leads are constructed as described above and as depicted in the drawings. The FPL 20 is approximately 26 cm in length from its proximal end 22 to its distal end 21. The FPL 20 has a distal non-stimulating tip of approximately 3 mm in length that abuts the FEA, which may have ten SME 24 uniformly disposed over approximately 8 cm. This is followed by an inter-array interval 27 of approximately 4 cm, then the PEA, which may include eight SME 24 uniformly disposed over approximately 6 cm, and finally a proximal lead segment 22a that ends at the proximal end 22, where the lead transitions to the IPG 10 and the lead internal wires 29, 38 connect to the ASIC 13.

In this embodiment, the occipital lead may comprise a plastic body member 39 over which six SME 34 may be disposed uniformly over approximately a 10 cm length of the lead, and the lead terminates in approximately a 3 mm distal non-stimulating tip 33.

In this embodiment, the IPG 10 comprises the elements described above and depicted in the drawings, including an ASIC 13, a rechargeable battery 12, and an antenna 11, which all may be housed in a medical grade metal can 15 with plastic cover 14. In this embodiment the dimensions of the IPG 10 measured along the outer surface of the plastic cover 14 may be approximately 5 cm by 3 cm by 0.5 mm.

The system includes a portable programmer and a portable recharging unit, both of which functionally couple to the IPG through a radiofrequency mechanism.

In this embodiment, the system is capable of handling a program from the portable programmer that includes such parameters as pulse amplitude, frequency and pulse width.

M. Alternate Embodiments

There are multiple alternate embodiments that preserve the features of the neurostimulation system disclosed herein, which include an externally rechargeable and programmable IPG, sized and configured for implantation in the head, and from which fronto-parietal and occipital leads, along with their respect surface metal electrode arrays, extend to cover multiple regions of the head. In various embodiments, the spacing and dimensions of the electrode array(s) may be constant, or the electrode arrays may be specifically designed with respect to electrode type, dimensions, and layout for improving the therapeutic effectiveness.

Thus, the disclosure comprises extended electrode array designs (two or more regions by a single lead), and/or multiple arrays and optimized intra-array electrode dispositions. The disclosure also comprises lead configurations, which include the capability of a modular lead design that provides for ports on either the standard FPL and OLs. In another embodiment, the IPG receive additional separate leads, if and as necessary either at the time of initial implant or in the future.

Further, the lead lengths, along with the specific technical makeup and dimensions of the individual surface metal electrodes and electrode arrays, may be varied to include more or less than three unilateral regions of the head (occipital, parietal, and frontal) contemplated by the first embodiment. For example, a single IPG may energize and control multiple additional leads of varying lengths that ultimately could be disposed over virtually every region of the head and face bilaterally.

At least two electrodes may be included per region, and while the first embodiment calls for a total of 24 electrodes disposed over three arrays covering three different regions of the head—the occipital, parietal and frontal regions—there is no absolute limit to the maxim number of electrodes. Similarly, while the first embodiment calls for three electrode arrays, the disclosure contemplates two, or even one array (so long as the array covers at least two regions). There is also no limiting maximum for the number of arrays. Also, there may be multiple variations of design within each separate array, including for example, variations in the number, dimensions, shape, and metal composition of the individual electrodes, as well as the distance and constancy of distance between electrodes, within each array. Further, each array may have the same or completely different designs.

While the neurostimulation system has been described for implantation as a peripheral neurostimulator in the head and for head pain, it is capable of being implanted and used as a peripheral nerve stimulator over other regions of the head and face than described above and also over other peripheral nerves in the body.

N. Operation

When functioning; that is when the internal circuit of lead internal wires is connected to an IPG; the SME of the various arrays are programmed to function as anodes and cathodes. The generated electrical pulse wave then passes from the ASIC of the IPG to the associated internal lead wire, and ultimately to its associated terminal surface metal electrode. The current then passes a short distance from the subcutaneous tissue to a contiguous, or nearby, electrode, whereby it passes back up the lead to its associated proximal metal contact, and then back to the IPG to complete the circuit. The generated pulse waves pass through the subcutaneous tissue between two terminal electrodes that stimulates the sensory nerves of the area. When active, the IPG may be programmed to produce continuous series of pulse waves of specified frequency, amplitude, and pulse width. It is this series of pulse waves actively stimulating a patient's locally associated nerves that underpins the therapeutic effect of the implanted unit. The electrical pulse wave then passes from a connected proximal surface metal contact, along the associated internal lead wire, and ultimately to its associated terminal surface metal contact.

It is to be understood that the implementations disclosed herein are not limited to the particular systems or processes described which might, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. In addition, the term "coupling" includes direct and/or indirect coupling of members.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

It will be appreciated by those skilled in the art having the benefit of this disclosure that this implantable head mounted neurostimulation system for head pain provides a unibody construction with implanted leads to cover the frontal, parietal, and occipital regions of the head. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An implantable neurostimulator for subcutaneous implantation in a position over a skull posterior to a pinna of a patient where an outer surface of the skull has curved contour having a first tangential plane at a first point and a second tangential plane at a second point, comprising:
   an implantable pulse generator (IPG), the IPG including a housing defining a housing interior volume, the housing having a major top surface and a shape that divides the housing into a first housing portion and a second housing portion, the housing interior volume including a first interior region within the first housing portion and a second interior region within the second housing portion, wherein:
      the first housing portion contains within the first interior region circuitry for generating stimulating signals, wherein the circuitry is disposed in a first plane corresponding to a substrate, and
      the second housing portion contains within the second interior region a coil for inductively receiving power, wherein the coil has a generally planar coil loop disposed in a second plane, and wherein the first housing portion is adjacent and non-overlapping the second housing portion, when viewed from a top side of the IPG toward the major top surface, the coil in the second housing portion being interfaced with the circuitry in the first housing portion;
   wherein, when the IPG is implanted in the position over the skull, the first plane associated with the first housing portion and the second plane associated with the second housing portion generally correspond to the first and second tangential planes of the outer surface of the skull, respectively, to generally conform to the curvature of the skull;
   a battery for being charged by the circuitry with inductive power received by the coil;
   a first lead having a first lead body interfaced with the circuitry in the first housing portion on a proximal end and having a first array of electrodes exposed to the exterior of the first lead body proximate a distal end thereof, each of the electrodes conductively and separately interfaced to the circuitry in the first housing portion through the first lead body to receive stimulating signals therefrom;
   a second lead having a second lead body interfaced with the circuitry in the first body on a proximal end and having a second array of electrodes exposed to the exterior of the second lead body proximate a distal end thereof, each of the electrodes conductively and separately interfaced to the circuitry in the first housing portion through the second lead body to receive stimulating signals therefrom; and
a coating disposed over the first and second housing portions and at least a portion of the first and second leads on the proximal ends thereof to form a unibody construction;
wherein the circuitry in the first housing portion is operable to drive the electrodes in the first and second arrays simultaneously, so that select ones of the electrodes can be driven to provide stimulating signals.

2. The implantable neurostimulator of claim 1, wherein the stimulating signals include pulsed signals.

3. The implantable neurostimulator of claim 2, wherein the stimulating signals pulse at predetermined frequencies.

4. The implantable neurostimulator of claim 1, wherein the first and second leads each include a plastic body member and a plurality of internal conducting wires.

5. The implantable neurostimulator of claim 4, wherein each of the electrodes is conductively interfaced with one of the internal conducting wires.

6. The implantable neurostimulator of claim 4, wherein the first and second leads are flexible.

7. The implantable neurostimulator of claim 1, wherein the electrodes in the first array on the first lead are disposed uniformly along a linear portion of the first lead at a first inter-electrode interval.

8. The implantable neurostimulator of claim 7, wherein the electrodes in the second array on the second lead are disposed uniformly along a linear portion of the second lead at a second inter-electrode interval.

9. The implantable neurostimulator of claim 8, wherein the first lead has a third array of electrodes, each of the electrodes of the third array conductively interfaced to the circuitry to receive stimulating signals therefrom.

10. The implantable neurostimulator of claim 9, wherein the third array of electrodes is disposed uniformly along a linear portion of the first lead at a third inter-electrode interval which is different than the first inter-electrode interval.

11. The implantable neurostimulator of claim 9, wherein the circuitry in is operable to drive the first, second, and third arrays simultaneously.

12. The implantable neurostimulator of claim 1, wherein the circuitry is operable to communicate wirelessly, via the coil, with a source external to the IPG.

13. The implantable neurostimulator of claim 1, wherein at least one of the electrodes is a cathode.

14. The implantable neurostimulator of claim 1, wherein at least one of the electrodes in each of the first and second arrays is an anode and another thereof is a cathode.

15. The implantable neurostimulator of claim 2, wherein the stimulating signals pulse at predetermined pulse-widths.

16. The implantable neurostimulator of claim 1, wherein the at least one of the electrodes is cylindrical in shape.

17. The implantable neurostimulator of claim 1, wherein at least one of the electrodes is flattened in shape.

18. A implantable neurostimulator for subcutaneous implantation in a position posterior and cephalad to a pinna and between an outer surface of the skull and overlying skin, where the outer surface of the skull has curved contour having a first tangential plane at a first point and a second tangential plane at a second point, comprising:
an implantable pulse generator (IPG), the IPG including a metal housing defining a housing interior volume, the housing having a major top surface and a shape that divides the housing into a first housing portion and a second housing portion, the housing interior volume including a first interior region within the first housing portion and a second interior region within the second housing portion, wherein:
the first housing portion contains within the first interior region an integrated circuit for generating stimulating signals, the integrated circuit being fabricated on a planar substrate, wherein the planar substrate corresponds to a first plane of the IPG,
the second housing portion contains within the second interior region a coil for inductively receiving power, the coil having a generally planar coil loop corresponding to a second plane, wherein the first housing portion is adjacent and non-overlapping the second housing portion, when viewed from a top side of the IPG toward the major top surface, the coil in the second housing portion being interfaced with the integrated circuitry in the first housing portion;
wherein, when the IPG is implanted in the position over the skull, the first plane associated with the first housing portion is generally parallel to the first tangential plane of the outer surface of the skull and the second plane associated with the second housing portion is generally parallel to the second tangential plane of the outer surface of the skull to generally conform to the curvature of the skull;
a battery for being charged inductive power received by the coil;
a first lead having a first lead body interfaced with the integrated circuit in the first housing portion on a proximal end and having a first array of electrodes exposed to the exterior of the first lead body proximate a distal end thereof, each of the electrodes conductively and separately interfaced to the circuitry in the first housing portion through the first lead body to receive stimulating signals therefrom;
a second lead having a second lead body interfaced with the circuitry in the first housing portion on a proximal end and having a second array of electrodes exposed to the exterior of the second lead body proximate a distal end thereof, each of the electrodes conductively and separately interfaced to the circuitry in the first housing portion through the second lead body to receive stimulating signals therefrom; and
a coating disposed over the first and second housing portions and at least a portion of the first and second leads on the proximal ends thereof to form a unibody construction;
wherein the circuitry in the first housing portion is operable to drive the first and second arrays simultaneously, so that select ones of the electrodes can be driven to provide stimulating signals; and
wherein the electrodes in each of the first and second arrays are programmed to function as anodes and cathodes.

19. The implantable neurostimulator of claim 18, wherein the circuitry disposed in the first housing portion is operable to communicate wirelessly, via the coil, with a source external to the IPG.

20. The implantable neurostimulator of claim 18, wherein the first and second leads each include a plurality of internal conducting wires, and each of the electrodes is conductively interfaced with one of the internal conducting wires.

* * * * *

UNITED STATES PATENT AND TRADEMARK OFFICE
CERTIFICATE OF CORRECTION

PATENT NO. : 10,946,205 B2
APPLICATION NO. : 15/979165
DATED : March 16, 2021
INVENTOR(S) : Reed et al.

Page 1 of 1

It is certified that error appears in the above-identified patent and that said Letters Patent is hereby corrected as shown below:

On the Title Page

On page 5, in Column 2, item (56) under "Other Publications", Line 12, delete "Jan. 8," and insert --Jan. 9,-- therefor In the Claims In Column 15, Line 41, in Claim 11, after "circuitry", delete "in"

In Column 15, Line 57, in Claim 18, delete "A" and insert --An-- therefor

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*